(12) United States Patent
Khuri et al.

(10) Patent No.: US 7,575,856 B2
(45) Date of Patent: Aug. 18, 2009

(54) COMPOSITIONS AND METHODS FOR THE EVALUATION AND RESUSCITATION OF CADAVERIC HEARTS FOR TRANSPLANT

(75) Inventors: Shukri Khuri, Westwood, MA (US); Hemant Thatte, Medfield, MA (US); Vladimir Birjinuik, Weston, MA (US)

(73) Assignees: The United States of America as represented by the Department of Veterans Affairs, Washington, DC (US); President and Fellows of Harvard College, Cambridge, MA (US)

( * ) Notice: Subject to any disclaimer, the term of this patent is extended or adjusted under 35 U.S.C. 154(b) by 256 days.

(21) Appl. No.: 11/261,860

(22) Filed: Oct. 28, 2005

(65) Prior Publication Data

US 2007/0098694 A1    May 3, 2007

(51) Int. Cl.
*A01N 1/02* (2006.01)
(52) U.S. Cl. .................... 435/1.2; 435/1.1; 436/63; 436/148; 436/163; 514/2; 514/18; 514/474
(58) Field of Classification Search ........... None
See application file for complete search history.

(56) References Cited

U.S. PATENT DOCUMENTS

| | | | | |
|---|---|---|---|---|
| 4,798,824 | A | 1/1989 | Blezer et al. | 514/60 |
| 5,407,793 | A | 4/1995 | Del Nido et al. | 435/1 |
| 5,476,763 | A * | 12/1995 | Bacchi et al. | 435/284.1 |
| 5,514,536 | A | 5/1996 | Taylor | 435/1.2 |
| 5,552,267 | A | 9/1996 | Stern et al. | 435/1.1 |
| 6,046,046 | A * | 4/2000 | Hassanein | 435/284.1 |
| 6,100,082 | A | 8/2000 | Hassanein | 435/284.1 |
| 6,567,679 | B1 | 5/2003 | Khuri et al. | 600/345 |
| 6,569,615 | B1 | 5/2003 | Thatte et al. | |
| 6,600,941 | B1 | 7/2003 | Khuri et al. | 600/345 |
| 7,186,210 | B2 * | 3/2007 | Feld et al. | 600/16 |
| 2003/0040665 | A1 | 2/2003 | Khuri et al. | 600/345 |
| 2006/0154358 | A1 * | 7/2006 | Hassanein et al. | 435/284.1 |

OTHER PUBLICATIONS

Olariu et al, European Journal of Echocardiography, Sep. 2003, vol. 4, No. 3, pp. 162-168.*
Green, "Understanding NSAIDs: From Aspirin to COX-2" Clinical Cornerstone (Sports Medicine), 2001, vol. 3, No. 5, pp. 50-60.*
Calne, R.Y. et al., "Trickle Perfusion for Organ Preservation," *Nature* 235:171-173 (1972).
Hickethier, Th. et al., "Ultrastructural investigations for reducing endothelial cell damage of vein grafts during CABG-operation and practical consequences," *J Cardiovasc Surg* 40:71-76 (1999).
Maurer, E. J. et al., "Comparison of UW and Collins Solutions for Preservation of the Rat Heart," *Transplantation Proceedings*, 22(4):548-550.
Rinia-Feenstra, M. et al., "Functional Properties of the Saphenous Vein Harvested by Minimally Invasive Techniques," *Ann Thorac Surg* 69:1116-20 (2000).
Swanson, D. K. et al., "Improved Heart Preservation with UW Preservation Solution," *Journal of Heart Transplantation* 7(6):456-467 (1988).
Lapenna D. et al., "Blood Cardioplegia Reduces Oxidant Burden In The Ischemic and Reperfused Human Mycocardium," *Ann. Thorac. Surg.* Jun. 1994; 57(6): 1522-5.
Okouchi, Y. et al., "Effectiveness of Modified University of Wisconsin Solution for Heart Preservation as Assessed in Heterotopic Rat Heart Transplant Model," *J Thorac Cardiovasc Surg* 1990:1104-8.
Oz, M.C., et al., "Novel Preservation Solution Permits 24-Hour Preservation in Rat and Baboon Cardiac Transplant Models," *Circulation* vol. 88, No. 5, Part 2, Nov. 1993.
Huk, I., et al., "L-Arginine Treatment Alters the Kinetics of Nitric Oxide and Superoxide Release and Reduces Ischemia/Reperfusion Injury in Skeletal Muscle," *Circulation* vol. 96, No. 2, Jul. 15, 1997.
Oshima et al., "Long-term heart preservation using a new portable hypothermic perfusion apparayus," *J. Heart and Lung Transplantation* 18:852-861 (1999).

* cited by examiner

*Primary Examiner*—L Blaine Lankford
*Assistant Examiner*—Allison M. Ford
(74) *Attorney, Agent, or Firm*—Medlen & Carroll, LLP

(57) ABSTRACT

The present invention describes devices, solutions, and methods for the ex-vivo assessment, resuscitation, triage, and maintenance of human candidate cadaveric hearts.

1 Claim, 2 Drawing Sheets

COMPOSITIONS AND METHODS FOR THE EVALUATION AND RESUSCITATION OF CADAVERIC HEARTS FOR TRANSPLANT

FIELD OF INVENTION

Generally, the present invention relates to the field of tissue preservation and organ transplantation. In one embodiment, the present invention relates to a solution for prolonged organ preservation, and more particularly to an aqueous solution for the preservation of hearts prior to transplantation. In one embodiment, the present invention describes devices and method for evaluating the prospective performance of a candidate cadaveric heart in advance of cardiac transplantation.

BACKGROUND

Tissue and organ preservation solutions have been designed to: i) lengthen the time a tissue or organ may be maintained, extra-corporeally, in a viable state and ii) maximize the performance of the tissue or organ following implantation in a recipient. Examples of these solutions include: a) the Stanford University solution (see, Swanson, D. K., et al., Journal of Heart Transplantation, (1988), vol. 7, No. 6, pages 456-467); b) modified Collins solution (see, Maurer, E. J., et al., Transplantation Proceedings, (1990), vol. 22, No. 2, pages 548-550; Swanson, D. K., et al.); and c) the University of Wisconsin solution (see, Belzer, et al., U.S. Pat. No. 4,798,824, issued Jan. 17, 1989).

Each of the above mentioned tissue or organ preservation solutions exerts a different effect on: i) the physiology and metabolism, during the period of ex vivo preservation, of a candidate tissue or organ and ii) the post transplant viability of said tissue or organ. Moreover, different protocols (for cardiac preservation) have been described using these solutions including: a) warm arrest/cold ischemia, b) cold arrest/macroperfusion, c) cold arrest/microperfusion, and d) cold arrest/cold ischemia.

This first method of cardiac preservation involves arresting the heart with a warm cardioplegic solution prior to exsanguination and cold preservation. This protocol, however, is not optimal given the rapid depletion of myocardial energy stores during the "warm" period.

The second method, which involves arresting the heart with a cold preservation solution, is better but continuous perfusion of the heart with traditional preservation solutions generates oxygen free radicals which can compromise the viability of the candidate tissue or organ after transplantation.

The third method, first described in the journal *Nature* in 1972 in a system called "trickle perfusion," also generates undesirable oxygen free radicals.

The fourth method, cold cardioplegic arrest of the candidate donor heart followed by immersion in a cold organ preservation solution, is currently the standard method of cardiac preservation. While this method creates a maximum six (6) hour "window of preservation"; preservation for more than four (4) hours is associated with a marked decrease in post transplantation viability.

Compounding these problems is the associated issue of organ availability. In the United States, all cardiac allografts are presently obtained from brain-dead, beating heart donors maintained on life support systems. As a result of this severely limited organ pool, 10%-40% of all cardiac transplant candidates die awaiting a new organ.

What is needed, therefore, is: i) a physiological solution that extends the amount of time a candidate organ remains viable for transplantation, and ii) methods and devices for evaluating the prospective performance of a candidate donor and/or cadaveric heart in advance of transplantation.

SUMMARY OF INVENTION

Generally, the present invention relates to the fields of tissue preservation and organ transplantation. In particular, the present invention (in selected embodiments) relates to solutions for prolonged organ preservation and, more particularly, to solutions used in a beating and non-beating heart preservation protocols. In selected embodiments, these solutions are used to resuscitate and preserve candidate cadaveric hearts and isolated portions of the vasculature. In one embodiment said cadaveric hearts are harvested in a beating state prior to transplantation. In another embodiment said cadaveric hearts are harvested from non-beating heart donors.

In other embodiments, the present invention relates to devices and methods for evaluating the prospective performance of a candidate cadaveric heart in advance of cardiac transplantation.

Adequate preservation of an organ intended for transplantation is critical to sustaining the organ's proper function following implantation. In selected embodiments, the present invention describes solutions that preserve organs, in a viable state, for periods of time greater than solutions currently in clinical use or solutions previously described in the literature. In a preferred embodiment, the present invention describes the preservation of hearts and isolated portions of the vasculature.

Embodiments of the present invention provide for extended preservation times for hearts and heart tissue. While it is not intended that the present invention be limited to any specific mechanism (or a specific perfusate temperature), maintaining hearts in a beating and substantially normothermic condition provides for preservation times well in excess of the four to six hours window of viability currently observed for arrested candidate cadaveric hearts maintained in an arrested hypothermic state. That is to say, maintaining a candidate cadaveric heart in the beating state serves (in part) to sustain normal metabolic, contractile, and endothelial function for periods of at least 10 hours, more preferably 20 hours, and most preferably in excess of 24 hours.

This extended preservation time, for ex vivo candidate cadaveric hearts, allow for: i) cross-matching of donor and recipient tissue types (which impacts the survival of a recipient of a transplanted organ) and ii) maintaining viability during extended transit times, thereby, expanding the geographic area from which organs may harvested. This, in turn, expands the number of prospective organ donors and recipients. While preferred embodiments of the present invention describe cadaveric hearts the solutions, protocols, and devices described in the instant application may be adapted to the preservation of other organs and tissues.

The devices, perfusion solutions, and methods described by the various embodiment of the present invention may be used to resuscitate and evaluate candidate cadaveric hearts. Moreover, it has been shown that a candidate cadaveric heart may be deemed competent for transplant (even after greater than 30 min of total arrest) if the RMA is greater than 6.5 (and more preferably greater than 6.8) and the left ventricular end diastolic pressure (herein after referred to as "LVEDP"), after electroconversion of a candidate cadaveric heart into a beating state, is maintained within a range between approximately 0.0-30.0 mmHg.

In one embodiment, the present invention describes a method of evaluating the viability of a candidate cadaveric heart comprising: providing an arrested candidate cadaveric heart; converting said arrested candidate cadaveric heart into a beating candidate cadaveric heart measuring the tissue pH of said beating candidate cadaveric heart and; using said measured tissue pH to evaluate the viability of said candidate cadaveric heart.

In one embodiment, the present invention describes a method of evaluating the viability of a candidate cadaveric heart comprising: providing an arrested candidate cadaveric heart; converting said arrested candidate cadaveric heart into a beating cadaveric heart; measuring: i) the pH of the anterior aspect of the myocardium and, ii) the LVEDP of said beating candidate cadaveric heart and; using said measured myocardial pH and said LVEDP to evaluate the viability of said candidate cadaveric heart. In one embodiment, said beating heart is in a functional rhythm. In one embodiment said functional rhythm is selected from the group consisting of sinus rhythm, nodal rhythm, and atrial fibrillation. In one embodiment, said candidate cadaveric heart is from a human.

In one embodiment, the present invention describes a method of treating a candidate cadaveric heart comprising: providing candidate cadaveric heart; measuring the tissue pH of said candidate cadaveric heart; and transplanting said candidate cadaveric heart into a recipient when, as measured in step b), the tissue pH is greater than 6.7. In one embodiment, said candidate cadaveric heart is beating.

In one embodiment, the present invention describes a method of treating a cadaveric heart comprising: providing an arrested cadaveric heart; converting said arrested heart into a beating cadaveric heart; measuring the LVEDP of said beating candidate cadaveric heart; and transplanting said candidate cadaveric heart into a recipient when said LVEDP is less than 30.0 mmHg. In one embodiment, said beating heart is in a functional rhythm. In one embodiment, said functional rhythm is selected from the group consisting of sinus rhythm, nodal rhythm, and atrial fibrillation. In one embodiment, said candidate cadaveric heart is from a human.

In one embodiment, the present invention describes a method of treating a candidate cadaveric heart comprising: providing an arrested candidate cadaveric heart; converting said arrested heart into a beating candidate cadaveric heart and; measuring: i) the tissue pH of said beating candidate cadaveric heart and ii) the LVEDP of said beating candidate cadaveric heart. In one embodiment, the present invention further describes a subsequent step comprising: transplanting said candidate cadaveric heart into a recipient when, as measured in step c), the tissue pH is greater than 6.8 and left ventricular end diastolic pressure is less than 30 mm Hg. In one embodiment, said beating heart is in a functional rhythm. In one embodiment, said functional rhythm is selected from the group consisting of sinus rhythm, nodal rhythm, and atrial fibrillation. In one embodiment, said candidate cadaveric heart is from a human.

In one embodiment, the present invention describes a method of treating a candidate cadaveric heart comprising: providing an arrested candidate cadaveric heart; perfusing said candidate cadaveric heart with a physiological solution; converting said perfused arrested candidate cadaveric heart into a beating heart and; measuring the pH of the anterior aspect of the myocardium of said beating candidate cadaveric heart. In one embodiment, the present invention further describes a subsequent step comprising: transplanting said cadaveric heart when the pH, measured in step c), is greater than 6.8 and LVEDP less than 30.0 mmHg. In one embodiment, said physiological solution consists of Hank's balanced salt solution, ascorbic acid, reduced glutathione, L-arginine, heparin, adenosine, guanosine, inosine, ribose, lipids, red blood cells, albumin, insulin, epinephrine and aspirin.

DEFINITIONS

Figure 1:
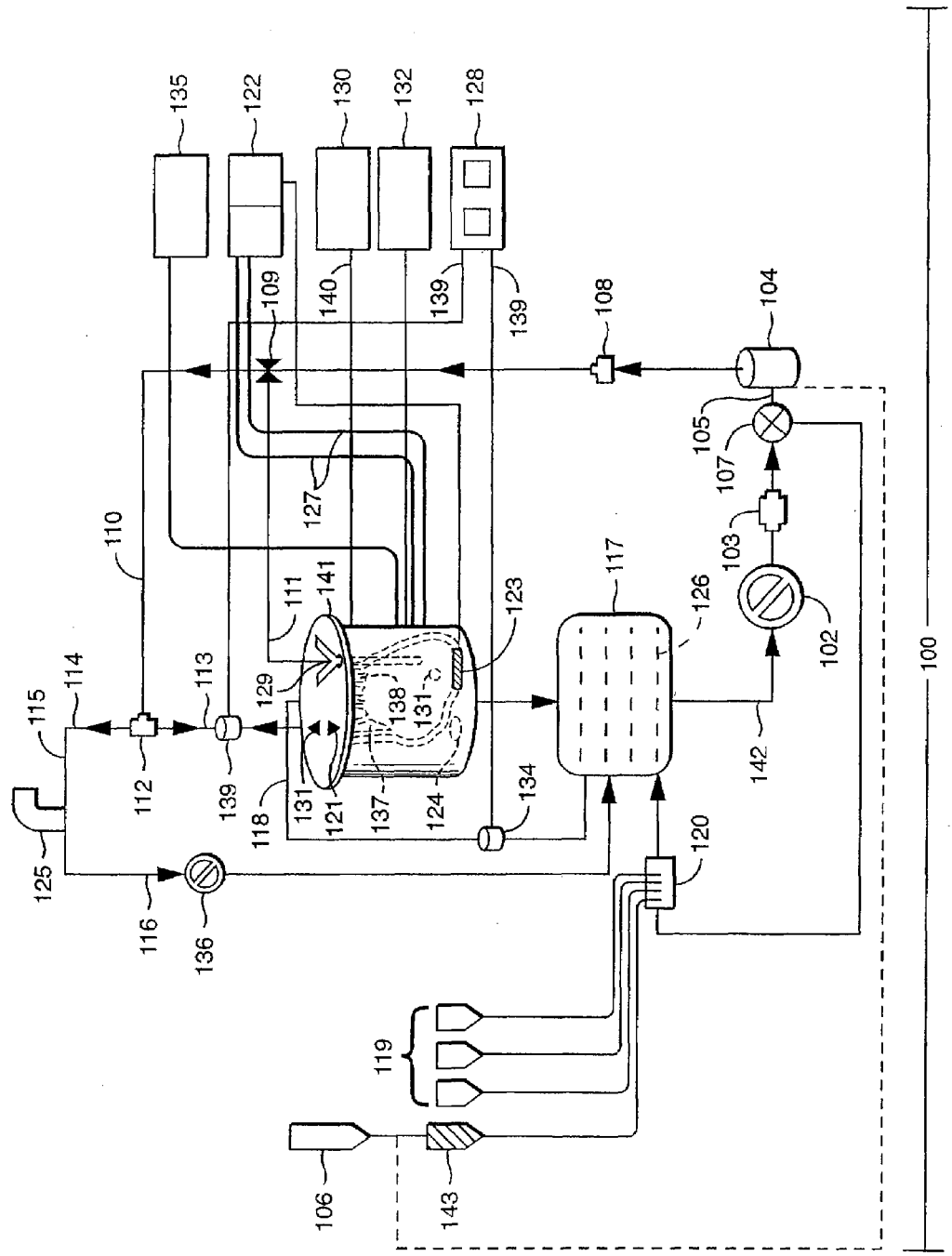
FIG. 1 shows a schematic of the containment and preservation system described by the present invention with a candidate cadaveric heart attached thereto.

As used herein, the term "patient" includes members of the animal kingdom including but not limited to human beings.

As used herein, "cardioplegia" refers to paralysis of the heart.

As used herein, an "antioxidant" is a substance that, when present in a mixture or structure containing an oxidizable substrate biological molecule, delays or prevents oxidation of the substrate biological molecule. For example, ascorbic acid is an antioxidant.

As used herein, a "balanced salt solution" is defined as an aqueous solution that is osmotically balanced to prevent acute cell or tissue damage.

As used herein, a "cardioplegia solution" is defined as a solution that aids in the preservation of the heart during transport or surgery.

As used herein, the term: "isolated portions of the vasculature" refer to portions of the vascular system that have been surgically harvested. Examples of isolated portions of the vasculature include (but are not limited to) aortic homografts, internal mammary arteries, and saphenous veins.

As used herein, a "physiological solution" is defined as an aqueous salt solution which is compatible with normal tissue, by virtue of being isotonic with normal interstitial fluid.

As used herein, a "candidate cadaveric heart" is defined as a heart harvested (from either a beating heart or non-beating heart donor) that is available for transplantation into a patient. In some embodiments, a candidate cadaveric heart includes varying lengths of the vessels that attach the heart to the circulatory system (e.g. the ascending aorta, the descending aorta, the inferior vena cava, the superior vena cava, the pulmonary arteries, and the pulmonary veins).

As used herein, the acronym "$LAP_{mpH}$" refers to the "Lower of the Anterior or Posterior Myocardial pH" as measured by pH electrodes in contact with the anterior and posterior wall of the atria or ventricles of the heart.

As used herein, the word "normothermic" refers the normal body temperature of a mammal. As an example, the normal body temperature of a human is in the range between approximately 36.0-38.0° C.

As used herein, the acronym "RMA" refers to: "Regional Myocardial Acidosis" which is defined as the lower of the measured anterior or posterior myocardial pH (i.e. the "$LAP_{mpH}$").

As used herein, the phrase "RMA within normal limits" refers to an RMA in a range between 6.5-7.8 and, more preferably, in a range between 6.8-7.2.

As used herein, the phrase "LVEDP within normal limits" or "normal LVEDP" refers to an LVEDP in the range of approximately 0.0-30.0 mmHg.

DETAILED DESCRIPTION OF THE INVENTION

I. The GALAH and GALAHS Solutions

The organ preservation solutions described by the present invention increase the amount of time an organ, intended for transplantation, may be preserved in a viable state. The organ preservation, or maintenance, solutions described by embodiments of the present invention shall be referred to as the "GALAH" solution (named after Glutathione, Ascorbic acid, L-Arginine for the Heart). This GALAH solution is a modification of the GALA solution taught in U.S. Pat. No. 6,569,615 to Thatte, et al. (herein incorporated by reference).

This GALAH solution, as described in embodiments of the present invention, differs from other organ preservation solutions in a number of respects. Crystalloid-based cardioplegic and preservation solutions (previously described in the literature) preserve the structural integrity and function of a candidate cadaveric heart in the range of four to six hours. Selected embodiments of the present invention describe formulations for solutions, including NOS substrates and antioxidants, which are easily prepared and are designed to preserve (in a preferred embodiment) a cadaveric heart.

Additionally, the preservation solutions described in various embodiments of the present invention do not require the elimination of sodium, calcium and chloride from the solution, as do many of the solutions described in the prior art (see, for example, U.S. Pat. No. 5,552,267 to Stern, et al.). In this regard, the preservation solutions described by selected embodiments of the present invention are improved over tissue preservation solutions described in the prior art.

In one embodiment, the GALAH solution of the present invention is based on Hank's balanced salt solution. Hank's balanced salt solution (HBSS) is a commercially available physiological salt solution containing D-glucose 1 g/L, calcium chloride (anhydrous) 0.14 g/l, potassium chloride 0.4 g/l, potassium phosphate 0.06 g/l, magnesium chloride.6$H_2O$ 0.1 g/l, magnesium chloride.7 $H_2O$ 0.1 g/l, sodium chloride 8 g/l, sodium bicarbonate 0.35 g/l, and sodium phosphate 0.048 g/l.

In a preferred embodiment, the GALAH solution of the present invention is prepared by supplementing HBSS with ascorbic acid (vitamin C), reduced glutathione, L-arginine, and heparin (in a preferred embodiment, these added compounds are adjusted to final concentrations of about 500 µM, 1000 µM, 500 µM, and 50 Units/ml, respectively) in addition to adenosine, guanosine, inosine, ribose, and an intralipid solution: i.e. a fatty acid emulsion which provides a additional source of metabolic energy to cardiac myocytes (in a preferred embodiment these additional compounds: adenosine, guanosine, inosine, ribose, and an intralipid solution are adjusted to final concentrations of about 1000 µM, 1000 µM, 1000 µM and 5000 µM and 20% respectively). There are many commercial sources for the compounds in the GALAH solution referenced above. One such source is the Sigma Chemical Company of St. Louis, Mo.

In some embodiments the GALAH solution, as described in the preceding paragraph, may be supplemented with additional water soluble vitamins (i.e. in addition to the native asocorbic acid in the solution), lipid soluble vitamins, and/or minerals (including, but not limited to selenium and zinc). In some embodiments, GALAH will be supplemented with Minocycline, an antibiotic (at a concentration of: 0.1-100 uMoles/L) that inhibits mitochondrial pore transition mediated Cytochrome C release from the mitochondria and thus protect against apoptosis.

In another embodiment this GALAH solution (with or without vitamin and/or mineral supplementation) is further supplemented with autologous or homologous purified and packed red blood cells (in a preferred embodiment with a final hematocrit in the range of 10-55%), human albumin (in one embodiment with a final concentration between: 1-20% and, in a preferred embodiment, with a 10% final concentration), insulin, which improves glucose uptake, (in one embodiment 5-100 units is added per 1 L volume of solution and, in a preferred embodiment, 40 units is added per 1 L volume of solution), epinephrine, a β 1 agonist which helps maintain sympathetic tone, (in one embodiment 5-10 mg is added per 1 L volume of solution and, in a preferred embodiment, 8 mg is added per 1 L volume of solution) and aspirin (in a preferred embodiment 40-200 mg is added per 1 L volume of solution), thereby, creating the GALAHS solution (i.e. GALAH "S" supplemented with one or more of the various compounds recited above).

While it is not intended the present invention is limited to any specific mechanism, the red blood cells in the GALAHS solution will keep the perfused cadaveric heart: i) oxygenated and ii) act as an oxygen sensor (regulating hypoxic vasodilatation and hyperoxic vasoconstriction via delivery of thiol and/or heme bound nitric oxide). The supplemented albumin will provide protection against cellular denaturation, while the nucleosides (provided in the form of triphosphates) will provide substrate to the cellular enzymes in the heart, thereby, providing a source of high energy phosphates (ATP, GTP, ITP) for cell function and contraction and relaxation of the heart muscle. Antibiotics, other hormones and pharmacological agents may also be added to the GALAH or GALAHS solutions. Both GALAH and GALAHS solution will (in selected embodiments) be: substantially isoosmotic, electrolyte stabilized, have low viscosity, be maintained, in a preferred embodiment, in a range of 20-37° C., and, in a preferred embodiment, have a final adjusted pH of approximately in the range between 6.8-7.8.

II. Evaluation of Candidate Cadaveric Hearts

A. Overview of Methodology

Another embodiment of the present invention is directed to the evaluation of cadaveric hearts which are candidates for transplant. A preferred embodiment of the present invention contemplates the evaluation of cadaveric hearts which have been harvested from both beating heart donors and non-beating heart donors (hereinafter referred to as "NBHDs").

In one embodiment, this evaluation protocol consists of: i) the antegrade reperfusion of a harvested heart, ii) the electroconversion (into a beating state) of said reperfused harvested heart, and iii) the subsequent measurement of: a) intracavitary pressures and/or b) measurement of myocardial pH in the anterior and posterior walls of the left ventricle. It is not intended that the measurement of myocardial pH be limited to a specific situs. That is to say, the measurement of the myocardial pH in the anterior and posterior walls of the right and ventricles and the right and left atriums are contemplated. In a preferred embodiment, these measurements (e.g. myocardial pH and/or intracavitary pressures) are used to predict the post-transplant performance of said candidate heart.

In a one embodiment, the above referenced anterior and posterior pH measurements are used to calculate regional myocardial acidosis (herein after referred to as "RMA"). Specifically, the RMA is defined by the lower of the measured anterior or posterior myocardial pH (i.e. the "$LAP_{mpH}$"). In one embodiment the RMA and the LVEDP, as measured in a candidate cadaveric heart, are combined to create an index which predicts the post-transplantation performance of said cadaveric heart. Specifically, in one embodiment, a candidate cadaveric heart with: i) an RMA greater than 6.6 and more preferably greater than 6.7 and most preferably greater than 6.8 and, ii) an LVEDP within a range of approximately 0.0-30.0 mmHg predict the successful performance, post-transplantation, of the cadaveric heart in question. In another embodiment, the RMA and LVEDP may be used independently predict the successful performance, post-transplantation, of the cadaveric heart in question.

In another embodiment, pH and LVEDP will be supplemented with additional measured parameters of cardiac myocyte function. That is to say, cardiac myocyte biopsies taken from the regions of pH electrodes (in a preferred embodiment, the anterior and posterior walls of the left ventricle) will be further evaluated by measuring: myosin, actin, mitochondrial respiration and polarization, ATP levels, esterase activity and membrane permeability (a measure of structural and functional viability), calcium mobilization, eNOS function, and nitric oxide generation. In some embodiments apoptosis and necrosis of cardiac myocytes will be evaluated using fluorescence based assays, immunofluorescence and multiphoton microscopy in transmission and/or epifluorescence mode, or by standard fluorescence/transmitted light microscopy, in presence of agonists and antagonists. That is to say, if a candidate cadaveric heart with an RMA and LVEDP within normal limits also presents chemistries and morphologies (as measured and observed in the aforementioned biopsy samples) substantially within normal limits, these biopsy data will further predict the favorable post-transplantation performance (as predicted by the RMA and/or LVEDP) of the candidate cadaveric heart.

B. Source and Harvest of Candidate Cadaveric Hearts

In one embodiment, the present invention contemplates the evaluation of any candidate heart for transplant. That is to say, the triage methods described in embodiments of the present invention may be applied to candidate hearts that have been harvested from either beating heart or a NBHD.

Currently, in the United States and other parts of the world, all cardiac allografts are obtained from brain-dead/beating heart donors maintained on life support systems. However even hearts harvested from beating heart donors, and subsequently maintained in a cold cardioplegia solution prior to transplant, still can experience metabolic changes that compromise their viability and/or performance after transplantation. The present invention describes, in part, embodiments directed toward: i) an improved preservation solution and ii) methodologies for the pre-transplant evaluation of donor beating hearts.

NBHDs have been excluded from the pool of hearts available for transplant due to the deleterious ischemic changes that occur in the interim between the cessation, at death, of myocardial perfusion and the subsequent harvest of the NBHD. Embodiments of the present invention are designed to minimize these changes, evaluate their severity, and predict the suitability of the resuscitated NBHD for subsequent transplantation.

In one embodiment, the following protocol may be adapted to harvest both beating heart and NBHDs. Harvesting of the heart and all subsequent procedures are executed under sterile conditions. Through a midsternotomy the heart is removed by excising, 1) the aorta as far distally as possible, 2) the superior and inferior vena cavae with as much length as possible of each of these vessels, 3) the pulmonary artery beyond its bifurcation, 4) The superior and inferior pulmonary vein with as much length as possible for both the vessels. The order of excision will be as follows: As soon as the pericardium is opened the superior and inferior vena cavae are dissected as far distally as possible and divided after distal clamping. The innominate artery is then dissected as far distally as possible and excised. The afterload cannula from the perfusion apparatus (FIG. 1) is connected to the innominate artery and the aortic arch is clamped before takeoff of the left carotid artery. Through the cannula, 5 liters of GALAH solution containing heparin, tissue plasminogen activator (TPA), streptokinase, eurokinase (independently or in combination thereof) is flushed into the heart. Finally, the pulmonary artery and the pulmonary vein are excised and the heart is removed from the chest cavity of the donor.

In one embodiment, once the heart is excised, the pH electrodes (KHURI pH Monitoring System, Terumo) are placed in the anterior and posterior region of the left ventricle. Biopsy samples from the regions of the pH electrodes may be taken at this stage for physiological, biochemical and histopathochemical evaluation of the cardiac myocyte if required. The heart is placed in the perfusion chamber and subsequently connected to the perfusion apparatus as described below.

C. Candidate Cadaveric Heart Containment And Preservation System

Figure 2:
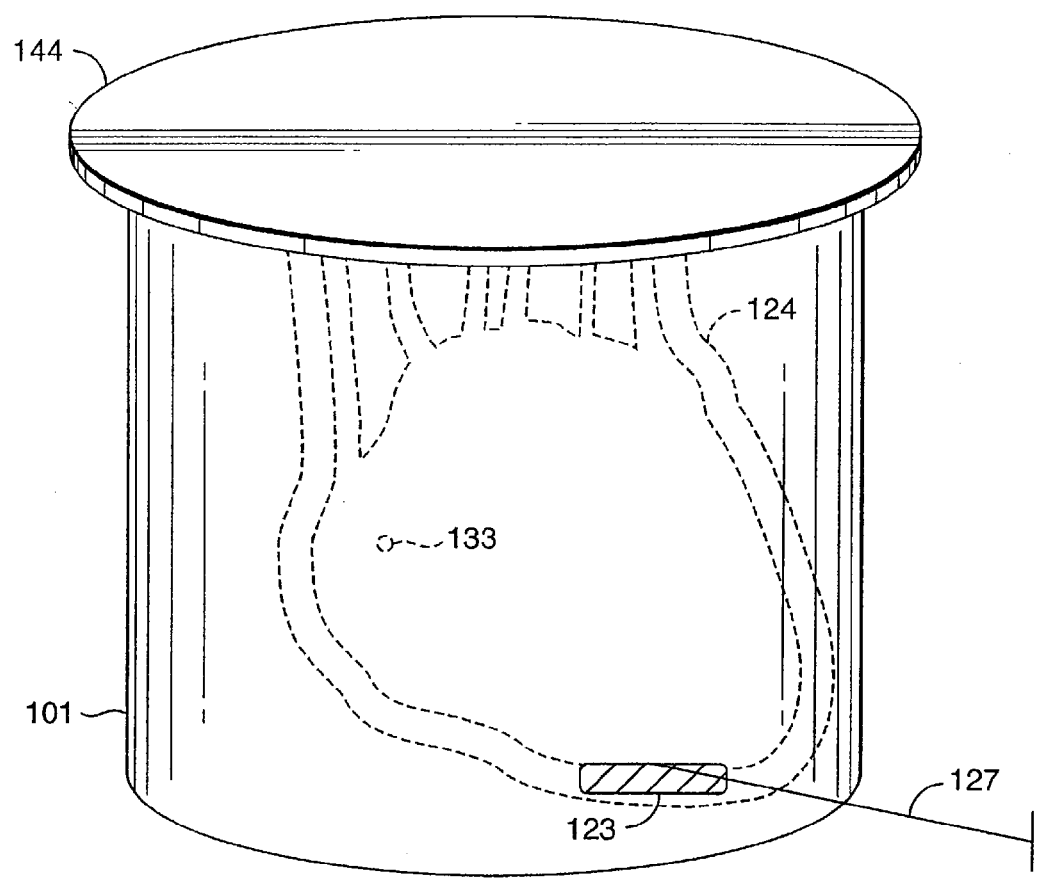
FIG. 2 shows an exploded view of the perfusion chamber 101 highlighting the connectivity between the semi-permeable membrane pouch 124 and the defibrillator pad 123.

While the present invention is not limited to any specific configuration, a schematic for one embodiment of a heart containment and preservation system is illustrated in FIG. 1. A candidate cadaveric heart 133, harvested from either a beating heart donor or a NBHD, is immersed in perfusion fluid 126 contained within the perfusion chamber 101. While it is preferred this chamber is fabricated from a hard plastic such as LEXAN, other materials are also contemplated. An exploded view of said perfusion chamber is set out in FIG. 2. In a preferred embodiment, this perfusion fluid is the GALAH solution which may be optionally supplemented with whole blood or blood products.

The centrifugal pump 102 (while it is not intended the components of the preservation system be limited to any specific model or manufacturer, in preferred embodiment the centrifugal pump is manufactured by Medtronics of Minneapolis, Minn.) is turned on delivering a pulsatile flow, thereby, circulating the perfusion fluid into an activated charcoal filter 103 that removes metabolites and debris from the perfusion fluid and then into a membrane oxygenator 104 and nitric oxide gas injector (when RBC and/or blood is used in the fluid). Unless otherwise stated, the perfusate 126 in the apparatus 100 remains in fluidic communication throughout the perfusion circuits via tubing 142. The fluid is oxygenated using a mixture of 95% oxygen and 5% carbon dioxide (1-2 L/min) by a membrane oxygenator 104 derived from a regulated oxygen bottle 105 (and nitric oxide is injected from a regulated nitric oxide bottle 106, when RBC and/or blood 143 is used, so as to maintained a nitric oxide concentration in the perfusate of 40-120 ppm). The plurality of ports on the oxygenator allows pressurized perfusion fluids to be directed to other devices as required. A water heater and/or heat exchanger 107 through a water circuit maintains the fluids within the perfusion circuit, in one embodiment, in a range of 20-37° C.

The warmed (or cooled) perfusion fluid then maintains the donor heart at desired temperature. The oxygenator output line carries the warmed, oxygenated fluid to a leukocyte filter 108 (in preferred embodiment, the leukocyte filter 108 is manufactured by Medtronics of Minneapolis, Minn.) for leukocyte depletion when blood or RBCs are a component of the perfusate. The output line of the filter carries the fluid to a selector valve 109, that directs the fluid to either initial perfusion line 110 (for antegrade perfusion via the aorta), the left atrium supply line 111 via the superior pulmonary vein (for antegrade perfusion via the left atrium), or both lines simultaneously for priming purposes. These lines (e.g. 110 and 111) form the arterial side of the circuit. The opposite end of the initial perfusion line 110 is connected to a tee 112 which branches to aorta line 113 and the afterload column line 114.

A straight line 115 connects the afterload line with the aorta return line 116. A one-way relief valve 125 can be provided in the straight line 115 to allow unidirectional pumping of the fluid from the afterload column line 114 through the straight line 115 into the aorta return line 116. The distal end of the after load line is attached to reservoir to allow fluids pumped through the aorta to flow back into the reservoir 117. The aorta line provide bi-directional flow from the donor heart depending on the mode of perfusion. The height of afterload column line 114 can be adjusted in order to selectively change the afterload pressure against which the heart will beat or pump. In another embodiment, a centrifugal pump 136 can be integrated into the aorta return line 116 to regulate the afterload pressure, instead of having to manipulate the height of the afterload column line 114.

The fluid pumped through the afterload column returns to the reservoir via the aorta return line 116. A right ventricle return line 118 is also connected to the pulmonary artery to return the coronary effluent to the reservoir 117. These lines form the venous return side of the circuit. Various IV bags/lines 119 (in a preferred embodiment, these bags and lines are manufactured by Baxter of Deerfield, Ill.) can be connected to a drip manifold 120 which is then connected to the reservoir 117 for enrichment and/or replenishment of the perfusion fluids, blood, blood products and various chemicals and pharmaceutical agents as required.

D. Maintaining Candidate Cadaveric Hearts in a Beating State

In one embodiment, the candidate cadaveric heart 133 is harvested (in either a beating or arrested state) preserving sufficient distal lengths of the aorta, pulmonary artery, superior and inferior pulmonary veins and superior and inferior vena cavae, so as to facilitate the various connections to the perfusion circuit as described above. It is not intended that the present invention be limited to any specific length of distal aorta, pulmonary artery and superior and inferior pulmonary veins and superior and inferior vena cavae. In a preferred embodiment, however, these vessels are greater than 2 cm in length. The candidate cadaveric heart is placed into the perfusion chamber 101 filled with perfusion fluid 126. The perfusion chamber is covered by a lid 144. It is not intended that the present invention be limited to a specific perfusion fluid. In one embodiment this perfusion fluid is GALAH. In another embodiment the perfusion fluid is leukocyte depleted whole blood. In another embodiment the perfusion fluid is the GALAH solution supplemented with whole blood. In another embodiment the perfusion fluid is the GALAH solution supplemented with packed red blood cells.

In one embodiment, after placement of the cadaveric heart into the perfusion chamber, remaining flow lines are connected to the candidate cadaveric heart. Specifically, the connection between aortic cannula 121 and aorta 137 is completed, supply line 111 is connected to the left atrium via the superior pulmonary vein 138 and the right ventricle return line 118 is connected to the pulmonary artery. It is not intended that the present invention be limited by the material used to facilitate the connection of a candidate cadaveric heart's vessels to the perfusion circuit. In one embodiment, however, silk suture is wrapped around a given vessel and gently cinched, by mean of a sliding knot, so as to create a ligature which compresses the lumen, of a vessel, around the external wall of the terminal portion of a perfusion line or cannula so as to create a seal. This seal is sufficient to substantially prevent peri-ligature flow of perfusate in the perfusion chamber 101. The superior and inferior vena cava are closed using, in one embodiment, a silk suture ligature. In one embodiment, these silk suture ligatures are 4-0 braded silk manufacture by the Ethicon Corporation.

In one embodiment, the centrifugal pump 102 is turned on, thereby, circulating perfusion fluid through the arterial side of the circuit. In one embodiment the temperature of said circulating perfusion fluid is regulated by the heat exchanger 107. In a preferred embodiment said heat exchanger regulates the temperature of said perfusion fluid in the range of 20-40° C. In another embodiment, said perfusion solution is oxygenated by an oxygenator 104. The circuit is primed by allowing the fluid to simultaneously pass through the initial perfusion line 110 and the left atrium supply line 111. Once the arterial lines are primed to remove any air bubbles, the valve 109 is rotated to direct the fluid through the initial supply line 110. Perfusion lines are connected to the aorta using an aortic cannula 121, thereby, allowing for immediate perfusion, via the aorta, of the candidate cadaveric heart which is (in one embodiment) in a non-beating state. At this stage, in a preferred embodiment, the afterload column line 114 is clamped to maximize perfusate flow into the aorta. In a preferred embodiment, this antegrade perfusion of the heart, via the aorta, is performed for approximately 15 minutes. During this time, baseline measurements from the various instruments measuring the physiological performance of the candidate cadaveric heart (including, but not limited to, LVEDP, Intracavity Pressure and myocardial pH) are recorded as the candidate cadaveric heart equilibrates in response to the antegrade perfusion. It is expected that the heart will start beating spontaneously during this period. If after 15 minutes of pH normalization the heart does not beat, it is then electrically cardioconverted.

In one embodiment after this equilibration period, the flow (of perfusate) to the aorta is reduced by rotating the selector valve 109 to the normal operating position, thereby, increasing the flow to the left atrium, via the left atrium supply line 111, and (reciprocally) gradually shutting off flow through the initial supply line 110. The afterload column line 114 is then unclamped. At this point, in most cases, the candidate cadaveric heart will convert from a non-beating to a beating state. However, in the event a candidate cadaveric heart fails to convert into a beating state (or is in an irregular rhythm) the candidate cadaveric heart may be electro-converted by passing current from an ECG/Automatic Defibrillator 122 (in preferred embodiment, the ECG/Automatic. Defibrillator 122 is manufactured by Medtronics of Minneapolis, Minn.) to a defibrillator pad 123 incorporated into the semi-permeable membrane pouch 124 against which the heart rests in the perfusion chamber 101.

In one embodiment, in addition to the perfusate flow to the heart provided by the native ejection fraction, as generated by a beating candidate cadaveric heart, perfusate flow to the heart may be supplemented by the pump 102. In a preferred embodiment the beating cadaveric heart is allowed to beat against an afterload pressure created by the force generated by the column of perfusate contained in the vertically oriented afterload column 114 which is positioned above the perfusion chamber 101, thereby, facilitating a pulsatile coronary flow.

In preferred embodiments of the present invention; the action potential, electrical activity, and mechano-contractile function of a candidate cadaveric heart is monitored by ECG via lines 127 attached to the right atrium and right ventricle. An automatic defibrillator 122 connected to a defibrillator pad 123, incorporated into the pouch 124 against which the heart rests in the chamber, resuscitates the heart as needed. The same lines 127 used monitor the mechano-contractile function of a candidate cadaveric heart may conduct a defibrillating pulse to the heart. That is to say, should the candidate cadaveric heart go into an irregular rhythm or arrest, the defibrillator may be programmed to discharge an electrical pulse (or pulses) which is likely to convert the candidate cadaveric heart from the irregular rhythm or arrest (as recorded by the ECG). The aortic flow is measured by an inline ultrasonic flow probe 134 that is a part of the aorta line. Similarly, an inline ultrasonic flow probe 134 measures the coronary blood flow through the right ventricle return line of coronary effluent from the right ventricle to the reservoir. Both, signals from these probes, transmitted via connecting wires 139, are recorded on a two-channel flow meter 128, which further assists in monitoring the performance of the candidate cadaveric heart.

In another preferred embodiment, the perfusion circuit described above provides oxygenated perfusate to the coronary vascular system, while the de-oxygenated fluid from the coronary vasculature is pumped from the right ventricle into the pulmonary artery return line and returned to the reservoir 117 where it is subsequently pumped through the oxygenator and is, thereby, re-oxygenated.

In one embodiment if the myocardial pH and left ventricular filling pressures of the perfused beating candidate cadaveric heart reach physiological levels, the candidate cadaveric heart is deemed competent for transplant. At this point, a recipient may be surgically prepared to receive the competent cadaveric heart. The competent cadaveric heart is kept perfused, in the beating state, until such time as the recipient is ready to receive the competent cadaveric heart and then the competent cadaveric heart is disengaged from the perfusion apparatus and transplanted into the recipient.

In this respect the device and methods described above allow for the triage, storage, and transportation of a competent cadaveric heart to the site of transplant.

E. Physiological Measurement Used to Evaluate Post Transplantation Performance of a Candidate Cadaveric Heart As discussed in preceding sections, selected embodiments of the present invention exploit the observation that a set of physiological parameters correlate with the post transplantation performance of a candidate cadaveric heart. That is to say, an RMA above 6.8 with a concurrent normal LVEDP comprise an output of measured physiological parameters which positively correlate with the normal post-transplantation performance of a candidate cadaveric heart.

In one embodiment a micro-tip pressure catheter 129 connected, via connecting wire 140, to pressure recording system 130 (in preferred embodiment, the pressure recording system 130 is manufactured by Medtronics of Minneapolis, Minn.) and is inserted into the left ventricle via the left atrium for measuring the intracavity pressure of the candidate cadaveric heart. The coronary flow is maintained within a physiological range (300-500 ml/min) by adjusting the height of the afterload column 114 above the heart and by adjusting the flow rate provided by the pump 102. In one embodiment of the present invention, the afterload pressure is maintained at approximately 70-80 mm mercury.

In one embodiment tissue pH, monitored continuously, is used as a functional measure of the integrity of hemodynamic, contractile, metabolic and microvascular processes during preservation of the candidate cadaveric heart. Specifically, RMA is defined in terms of the $LAP_{mpH}$. These pH measurements were made by inserting tissue pH electrodes 131 (as described in U.S. patent application 2003/0040665 A1 to Khuri et al., U.S. Pat. No. 6,567,679 B1 to Khuri et. al., and U.S. Pat. No. 6,600,941 B1 to Khuri et al., hereby, incorporated by reference) into the anterior and posterior ventricular walls of a candidate cadaveric heart. The reference electrode 131 will be placed in the dedicated pH probe port in the tubing and/or cannula 121 that is attached to the aorta. These electrodes are connected to a pH monitor 132 (in preferred embodiment, the pH monitor 132 is the KHURI Myocardial pH Monitoring System manufactured by Terumo Cardiovascular Systems of Ann Arbor, Mich.) which gives a discrete read out of the myocardial pH in the anterior and posterior ventricular walls of the candidate cadaveric heart.

In a preferred embodiment, a candidate cadaveric heart is deemed to be competent for transplant when a candidate cadaveric heart (restored to a beating state in the apparatus described above) meets the following criteria. First, in one embodiment, the RMA is in a pH range between approximately 6.60 and 7.60. In a preferred embodiment RMA is in a pH range between 6.90 and 7.20. Second, measured LVEDP is in a range between 0 and 30.0 mmHg (as measured by the LVEDP monitor 135). In a preferred embodiment said measured LVEDP is in a range between 0-12 mmHg. It is not intended that the present invention be limited to a specific amount of reperfusion time (in the apparatus described above) prior to determining that a candidate cadaveric heart is (or is not) competent for transplant. In a preferred embodiment, the optimal RMA and LVEDP (described above) will be observed after two hours, or less, of reperfusion. However, longer reperfusion times (e.g. 2-6 hours) are also contemplated before RMA and LVEDP reach levels which predict for good post-transplantation performance.

In one embodiment, ventricular biopsies using the integrated punch biopsy instrument 141, will be taken from the regions of the pH electrode insertion points for additional physiological, biochemical and histopathochemical evaluation.

EXPERIMENTAL

The following example is offered as an exemplar of one embodiment of the present invention. However, it is not intended that the scope of the present invention be limited by any specific element in the following example.

12 adult pigs were exsanguinated, thereby, inducing an ischemic cardiac arrest followed by 30 minutes of in-vivo ischemia. Hearts were then excised according to the protocol previously described. These harvested hearts were and reperfused (according to the protocol described above) using autologous, leukocyte-depleted blood as the perfusate. To summarize, hearts were perfused antegrade in the non-working state for a 20-minute period of stabilization and instrumentation, after which hearts were electroconverted, using DC shock, to the beating working state. Ventricular arrythmias were corrected using DC shock.

Intracavitary pressures were monitored using micro-tip pressure transducer. In addition, endothelial vasomotor function was assessed by generating dose responses of coronary rings to bradykinin and nipride. Myocardial pH was continuously measured in the anterior and posterior walls of the left ventricle throughout the experiment using the Khuri myocardial tissue electrodes (as described in U.S. patent application 2003/0040665 A1 to Khuri et al., U.S. Pat. No. 6,567,679 B1 to Khuri et. al., and U.S. Pat. No. 6,600,941 B1 to Khuri et al., hereby, incorporated by reference). It is also contemplated that the GALAH solution may be used as an alternative perfusate.

10 of 12 hearts were successfully converted into a beating state. After two hours of reperfusion, LV developed pressure was 89±6 mmHg (mean±standard deviation) and spontaneous rhythm was sustained at a heart rate of 128±7 BPM. Endothelial vasomotor function was completely preserved as evidenced by the dose response relaxation to bradykinin $10^{-8}$M compared to controls (44, 42 change from baseline, P>0.05). A similar correlation was observed for coronary smooth muscle function, as evidenced by the dose response to nipride $10^{-6}$M (27, 22% change from baseline, P>0.05).

For each isolated heart, the magnitude RMA was defined in terms of the lower of the anterior or posterior myocardial pH ($LAP_{mpH}$). In the whole study, $LAP_{mpH}$ at end of reperfusion was 7.09±0.45 (mean±standard deviation). Prior to the Starling curve, $LAP_{mpH}$ was 6.99±0.33 and at end of the curve it remained statistically unchanged at 7.01±0.44.

The two isolated hearts that could not be successfully converted to the working model both exhibited RMA pH<6.8. Two of the resuscitated hearts exhibited RMA <6.8 at end of reperfusion. In both, the Starling curve showed marked deterioration of LV function exhibited by a marked reduction in the developed pressure and an elevation of the LVEDP. $LAP_{mpH}$ at end of the starling curve was markedly lower than at the beginning in both hearts.

The invention claimed is:

1. A method of treating a candidate cadaveric heart comprising:
    a) providing an arrested candidate cadaveric heart;
    b) perfusing said candidate cadaveric heart with a physiological solution, wherein said physiological solution consists of Hank's balanced salt solution, ascorbic acid, reduced glutathione, L-arginine, heparin, adenosine, guanosine, inosine, ribose, lipids, red blood cells, albumin, insulin, epinephrine and aspirin;
    c) converting said perfused arrested candidate cadaveric heart into a beating heart;
    d) measuring the pH of the anterior aspect of the myocardium of said beating candidate cadaveric heart, and
    e) transplanting said cadaveric heart when the pH, as measured in step d), is greater than 6.8 and a left ventricular end diastolic pressure is less than 30 mmHg.

* * * * *

UNITED STATES PATENT AND TRADEMARK OFFICE
CERTIFICATE OF CORRECTION

PATENT NO. : 7,575,856 B2  Page 1 of 1
APPLICATION NO. : 11/261860
DATED : August 18, 2009
INVENTOR(S) : Khuri, Birjiniuk and Thatte It is certified that error appears in the above-identified patent and that said Letters Patent is hereby corrected as shown below:

On the Title Page, Item (75)

The Applicant's name was spelled Birjinuik.

The Applicant's name should be spelled Birjiniuk.

Signed and Sealed this

Ninth Day of February, 2010

David J. Kappos
*Director of the United States Patent and Trademark Office*